(12) United States Patent
Van der Zel

(10) Patent No.: US 7,686,989 B2
(45) Date of Patent: Mar. 30, 2010

(54) METHOD FOR MANUFACTURING A DENTAL RESTORATION

(75) Inventor: Joseph M. Van der Zel, Hoorn (NL)

(73) Assignee: Degudent GmbH, Hanau (DE)

( * ) Notice: Subject to any disclaimer, the term of this patent is extended or adjusted under 35 U.S.C. 154(b) by 362 days.

(21) Appl. No.: 10/474,605

(22) PCT Filed: Apr. 19, 2002

(86) PCT No.: PCT/NL02/00259

§ 371 (c)(1),
(2), (4) Date: Mar. 16, 2004

(87) PCT Pub. No.: WO02/085242

PCT Pub. Date: Oct. 31, 2002

(65) Prior Publication Data

US 2004/0145070 A1 Jul. 29, 2004

(30) Foreign Application Priority Data

Apr. 23, 2001 (NL) .................................. 1017907

(51) Int. Cl.
*A61C 13/00* (2006.01)
*B29C 35/08* (2006.01)
(52) U.S. Cl. .............................. 264/20; 264/16; 264/19; 264/113; 264/122; 264/245; 264/308; 264/460; 264/497; 264/482; 264/641; 264/681; 433/203.1
(58) Field of Classification Search .................. 264/16, 264/19–20, 113, 400, 482
See application file for complete search history.

(56) References Cited

U.S. PATENT DOCUMENTS 5,219,805 A 6/1993 Yoshida et al.
5,768,134 A * 6/1998 Swaelens et al. ............ 700/121
5,823,778 A * 10/1998 Schmitt et al. .............. 433/214
6,322,728 B1 * 11/2001 Brodkin et al. ............... 264/19
6,713,421 B1 * 3/2004 Hauptmann et al. ......... 501/103
6,808,659 B2 * 10/2004 Schulman et al. ............. 264/16
6,955,776 B1 * 10/2005 Feenstra ....................... 264/16

FOREIGN PATENT DOCUMENTS

| CA | 2295896 | * 7/2000 |
|---|---|---|
| DE | 42 07 179 A1 | 9/1992 |
| DE | 199 38 143 A1 | 2/2001 |
| EP | 1 021 997 A2 | 7/2000 |
| NL | 1007059 | 10/1998 |
| WO | WO 01/13814 A1 | 3/2001 |

* cited by examiner

*Primary Examiner*—Jeffrey Wollschlager
(74) *Attorney, Agent, or Firm*—The Webb Law Firm

(57) ABSTRACT

A method for manufacturing a dental restoration, including: determining an external form and dimensions available for a completed restoration; obtaining an image of a natural tooth to be replaced with the restoration or a tooth corresponding therewith, wherein the image comprises at least the external surface visible in use of the to be replaced or corresponding tooth, with variations in the appearance therein; defining locally on and at least to visible depth below the surface of appearance-determining properties of at least one material to be applied for the restoration in accordance with the obtained image and the variations in the appearance therein; constructing the restoration, including the steps of: providing at least one material to be applied in non-cohesive form; and providing cohesion to the material in accordance with the available form and dimensions.

5 Claims, 1 Drawing Sheet

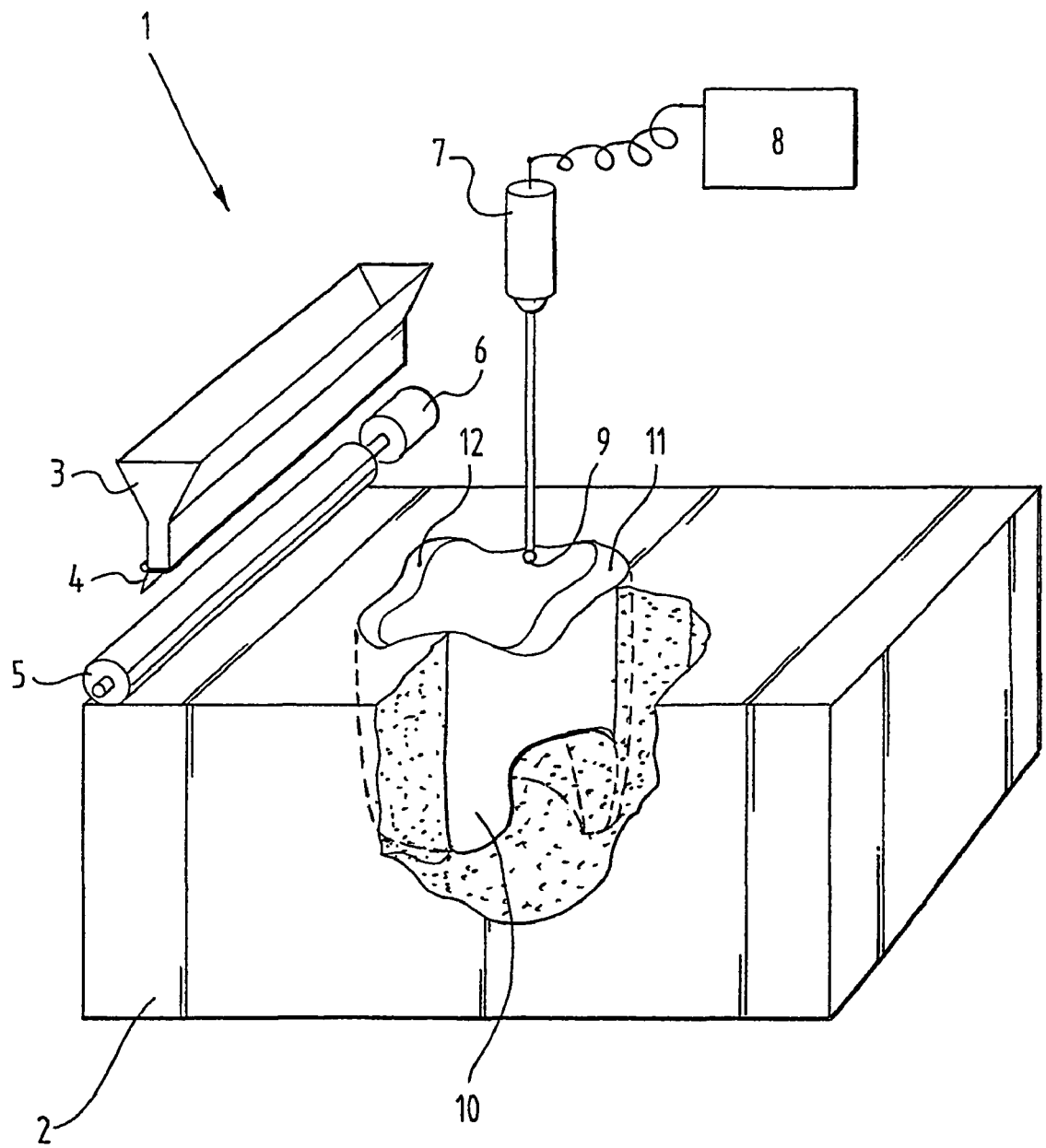

METHOD FOR MANUFACTURING A DENTAL RESTORATION

BACKGROUND OF THE INVENTION

1. Field of the Invention

The present invention relates to a method for manufacturing a dental restoration.

2. Description of the Related Art

Different methods are known in the art for manufacturing a dental restoration, wherein these methods are mainly determined by the type of materials used.

Ceramic materials have been successfully applied for many years in dental restorations. The two most important functions of restorative ceramics are aesthetics and strength. However, most dental ceramics do not fulfil both functions. Different porcelains and glass ceramics are used for aesthetic applications. These have a natural tooth colour and translucence but have a relatively low three-point bending strength (50-200 MPa).

Higher-strength materials have been developed as basic core material. These materials have a three-point bending strength of 150 to 500 MPa, but are generally too opaque and must be combined with translucent porcelain veneered thereon. The fracture toughness however remains low compared to metal alloys, whereby these ceramics are susceptible to production errors and stress concentrations, such as occur when there is a less than optimal fit between prepared tooth and the restorative ceramic.

Medically pure yttrium-stabilized tetragonal zirconium oxide (Y-TZP) is characterized by both aesthetics and a high three-point bending strength, higher than 1000 MPa, with a great toughness and an excellent resistance to slow crack development. Zirconium oxide has heretofore been applied very successfully in orthopaedics as hip-joint ball. It has also been very successfully introduced in dentistry for root pins. It has further been found to have a very low susceptibility to dental plaque. However, zirconium oxide has a white colour not suitable for dental restorations and must be coloured with a colour corresponding with the tooth colours.

In DE 4207179 A1 (1992) Yoshida describes a method of colouring orthodontic zirconium oxide components by adding a mixture of erbium-, praseodymium-, iron- and zinc oxides. Some additives, such as zinc, result in serious degradation of the physical properties of the sintered zirconium oxide. In DE 19938143 A1 erbium-, iron- and manganese oxide are mainly applied as colouring oxides.

Effect of suitable colour additives to sintered Y-TZP zirconium oxide

| Colour additive | Form | Effective colour | Note |
| --- | --- | --- | --- |
| Iron | $Fe_2O_3$ | Brown | Concentration lower than 1% by weight |
| Erbium | $Er_2O_3$ | Light violet | Forms solid solution with $ZrO_2$ |
| Praseodymium | $Pr_2O_3$ | Deep yellow | Forms solid solution with $ZrO_2$ |

These are first dissolved in hydrochloric acid and added to zirconium oxide and admixtures dissolved in hydrochloric acid. By hydrolysis with ammonia, annealing of the deposition and fine-grinding, an homogeneously coloured zirconium oxide powder is obtained which can be further processed. This takes place by mixing the powder with binders (for instance 2% by weight polyvinyl alcohol and 0.15% by weight oleic acid), and making this into a geometrical shape by pressing. The binder is burnt out for 0.5 to 2 hours at a temperature of 850-1000° C. A dental restoration, enlarged by the sintering shrinkage factor, is then cut out by means of a CAD/CAM system and the product is sintered to increase density at 1300-1500° C. for 2-4 hours. The result is a monochrome coloured restoration.

It is however desired in dentistry to colour the restoration locally. The base structure of a crown, in the form of a cap, is thus coloured slightly browner at the bottom, the so-called shoulder portion, and lighter yellow in the sections in the cutting edge area.

At the moment the restorations are further produced in automatic manner with fairly traditional cutting technique, with proportionately high material loss. With the use of zirconium oxide the price of the material is considerable and a net-shape production method would be desirable. Accurate colouring with locally occurring variations is complex here, if not impossible.

Up to the present there has been no possibility of making restorations using rapid prototyping or even in automated manner which have locally different properties or colours. In addition to the absence of an experimental configuration, there has also been no possibility of locally colouring product files.

In order to obviate or at least reduce the above stated and other problems and drawbacks of the known art, a new method for manufacturing a dental restoration is provided according to the present invention.

SUMMARY OF THE INVENTION

With a method according to the invention it is possible to manufacture a restoration with a very natural appearance, in respect of both colour, translucence and so on and the shape thereof.

A possible embodiment of a method according to the invention can be designated as 3D printing. Experimental configurations have recently been constructed, particularly at the Massachusetts Institute of Technology (MIT, Boston, USA), with which it is possible using software to determine the colours of the STL files (input files for rapid prototyping machines). Owing to the development of new materials and machines, the possibilities in the field of 3D printing have recently been greatly expanded, although there is still no application known for using this technology for dental restorations. The printer is used to apply an organic binder to a powder compacted using a roller, whereby complex shapes can be produced.

The principle of 3D printing (3DP) is known. The method was developed by the institute of technology of Boston, MIT. Market developments of the principle have since taken place. Zcorporation for instance has however used starch, which has little environmental impact and is freely available, as binder.

A drawback to the use of starch as binder is that it increases the shrinkage of the bound ceramic powder and that the shrinkage can moreover not be predicted in all directions. This makes starch less useful for the accuracy desired in dentistry. This in contrast to cold isostatic pressed (more than 2000 bar) ceramic, which after cutting and sintering results in a sufficiently accurate restoration. A new material, ZP100, was developed as an alternative, with which thin-walled and complex products such as dental restorations can indeed be printed in 3D with sufficient accuracy.

It is furthermore possible to "build in" a natural colour layer by layer by adding Pr-oxide (yellow), Fe-oxide (brown) and Er-oxide (violet) as pigment to the binder. The quantities to be applied amount for each of these colour additives to between for instance 0.05% and 2.0% of the weight.

In a preferred embodiment a method according to the invention, by providing the material layer by layer, the depth to which this material must be processed to provide it with cohesion remains limited. The production process hereby remains readily manageable and leads to good results. Particularly good results are achieved in respect of the appearance of the restoration to be produced (colour, translucence and so on), if certain measures are herein also applied. Colour variations can thus be realized in a three-dimensional direction over the outer surface of the restoration to be produced, while colour variations could only be realized in the direction in which the layers are successively provided on each other when layers to be provided separately have a homogeneous composition. A variation resulting in colour variation can also be realized in the layers, so that even more natural variations can be obtained.

In yet another preferred embodiment the non-cohesive form of the material to be applied can be one of powder form, liquid, thin slices and so on. This is related to the method to be applied for providing cohesion therein. In a powder form the cohesion can for instance be given by selectively adding binder to the powder or by subjecting the powder to the action of at least one laser. Particularly in the case of liquid forms of the material to be applied, an arrangement with two lasers can be used depending on the capacity of this liquid material to transmit laser light, where the intended effect of providing cohesion, for instance solidifying, only occurs where the laser beams coming from the lasers cross each other. In an embodiment with thin slices colour variations can be realized per slice around the periphery thereof, or the slices can be manufactured from homogenous material.

The material to be applied in the method is for instance ceramic material, porcelain, glass ceramic, and so on, but preferably yttrium-stabilized tetragonal zirconium oxide, to which the invention is however not limited. This has properties which are very advantageous in respect of the invention.

In order to allow variation in the appearance over the outer surface of the restoration to be manufactured, for instance in respect of the colour thereof, many materials can be used, such as erbium oxide, iron oxide and praseodymium oxide, manganese oxide and so on. Such materials can be combined well with the materials to be applied in the restoration to be manufactured, particularly zirconium oxide.

The present invention will be elucidated on the basis of an embodiment hereinbelow and a description of the one annexed drawing, which shows schematically a partly cut-away perspective view of an embodiment of the invention.

BRIEF DESCRIPTION OF THE DRAWINGS

The FIGURE shows a possible embodiment of an installation as implementation of the present invention.

DETAILED DESCRIPTION OF THE INVENTION

Installation 1 comprises a holder (not shown) in which layers of powder-form yttrium-stabilized tetragonal zirconium oxide (Y-TZP) can be placed one over another. The zirconium oxide is in powder form so that a body 2 of this powder is formed as the stacking of said layers onto each other progresses.

The layers are arranged using a powder holder 3, which in this embodiment is funnel-shaped and adapted to pour a measured quantity. Powder holder 3 is provided for this purpose with a flap 4 with which the pouring opening of powder holder 3 can be closed.

If a quantity of powder-form zirconium oxide from powder holder 3 is poured, either at one location or spread over the upper surface of the body 2 formed so far, the upper surface is leveled using a driven roller 5 which is coupled to a motor 6. The powder-form zirconium oxide is not only leveled, but also compressed and compacted to the desired extent.

The installation further comprises a laser generator 7 connected to a control 8. The focal point 9 of the laser generator acts on the upper surface of body 2 to give the powder-form zirconium oxide cohesion in the upper layer, which has just been poured from powder holder 3 and leveled and compacted by roller 5. Under the influence of the action of the focal point of laser generator 7 there also occurs adhesion to the material lying beneath the last poured layer. Any random shape can thus be generated in a layered structure, precisely this being advantageous in the case of dental restorations because of the usually erratic shapes thereof.

The FIGURE shows such a dental restoration 10. The method for manufacture hereof is being performed, so that the dental restoration 10 is only partly shown. A part of the body 2 of loose powder is further cut away in the view in order to show the dental restoration 10.

The focal point 9 of laser generator 7 follows a pattern in the material of the last spread layer such that, after processing a number of layers in this manner, a desired three-dimensional form of the dental restoration can be obtained.

In the areas 11 and 12 of the dental restoration 10 material is added to the powder-form zirconium oxide prior to the action of focal point 9. This may be for instance iron oxide, erbium oxide or praseodymium oxide. These materials have an effect on the colour, wherein iron oxide produces a brown discolouration and erbium oxide a light violet discolouration, while praseodymium oxide has a deep yellow colouring effect.

It is shown clearly in the FIGURE that, round the periphery on the upper side of the dental restoration 10 formed so far in the FIGURE, variations are arranged in the depth in internal direction of layers 11 and 12, which can otherwise also be doped with colouring agents differing from those stated above. Colour variation is thus possible in all directions over the outer surface of the dental restoration 10 to be formed. The properties of the material for doping in areas 11 and 12 can be varied from the bottom to the top, just as around the surface shown in the FIGURE of a cross-section of a dental restoration 10 to be formed.

The installation 1 shown in the FIGURE is also referred to as a colour printer.

As an alternative within the scope of the present invention to the laser generator 7 shown in the FIGURE, it is also possible to work with a binder which gives the non-cohesive powder-form zirconium oxide cohesion locally and where desired. As shown in the FIGURE, this can also take place in a structure with layers. The binder is active up to a depth to which the binder is able to give cohesion to the powder-form zirconium oxide. In such an application this active depth is of course greater than the thickness of a layer of powder-form zirconium oxide which has been applied or is to be applied, so that the adhesion to underlying parts of the restoration 10 to be formed is also brought about.

Dental restorations are manufactured with colour printer 1 from a loose, dry zirconium oxide powder with 3% yttrium oxide. The geometry for the restorations originates from a scan-design system such as a CAD-CAM system. Printer 1 is used to apply an organic binder to powder compacted with the roller, whereby complex shapes can be produced. A solution of 4% by weight 4AC (Hercules, USA) is made as binder. Three print suspensions are made herefrom by adding respectively 0.05% Pr-oxide, 0.05% Fe-oxide and 0.05% Er-oxide. The pigment is added to the binder as micronized powder and mixed in a turbine agitator. In a colour printer a bridge is imprinted with an STL data file, with differentiated colouring, obtained from a CAD system for dental restorations. After construction the bridge is heated to 650° C. at 5° C./min. The restoration is then heated to 1500° C. at 10° C./min and held there for 2 hours. The bridge exhibits the designed local differentiated colouring.

The invention claimed is:

1. A method for manufacturing a dental restoration, comprising the steps of:
    determining an external form and dimensions available for a completed restoration;
    obtaining an image of a natural tooth to be replaced with the restoration or a tooth corresponding therewith, wherein the image comprises at least the external surface visible in use of the to be replaced or corresponding tooth, with variations in the appearance therein;
    defining locally on and at least to a visible depth below the surface of appearance-determining properties of at least one material to be applied for the restoration in accordance with the obtained image and the variations in the appearance therein; and
    constructing the restoration, including the steps of: repeatedly providing layers of at least one material to be applied in non-cohesive form; and for each layer providing cohesion to the layer of at least one material with previous layers in accordance with the available form and dimensions,
    where the step of providing at least one material to be applied includes: varying the at least one material to be applied in accordance with variations in the image in a plane defined by each of the layers around the periphery of the surface of a layer cross section of the dental restoration to be formed,
    wherein the at least one material is in powder form including an additive configured to bring the appearance of the restoration to be formed into accordance with the image, the additive comprising at least one of the following: erbium oxide ($Er_2O_3$), iron oxide ($Fe_2O_3$), praseodymium oxide ($Pr_2O_3$) and manganese oxide ($Mn_2O_3$),
    wherein the step of applying the cohesion is performed by sintering of the powder without the use of a binding additive and by an action of a laser.

2. The method as claimed in claim 1, further comprising the steps of providing layer by layer in non-cohesive form at least one material to be applied; and providing cohesion to the material in each of the layers in accordance with the available form and dimensions as well as providing adhesion to a preceding layer before providing a subsequent layer.

3. The method as claimed in claim 1, including providing as the material to be applied at least one of ceramic material, porcelain, glass ceramic and yttrium-stabilized tetragonal zirconium oxide (Y-TZP).

4. The method as claimed in claim 2, further comprising the step of leveling a provided layer of material, prior to providing the material with cohesion.

5. The method as claimed in claim 1, wherein the determining step is performed using a CAD-CAM system.

* * * * *